US012653854B2

(12) United States Patent
Shade et al.

(10) Patent No.: US 12,653,854 B2
(45) Date of Patent: Jun. 16, 2026

(54) INTRA-ORAL NANOEMULSION INCLUDING MONOLAYER SURFACTANT BOUND PARTICLES FOR BALANCING HISTAMINE RESPONSE

(71) Applicant: Quicksilver Scientific, Inc., Louisville, CO (US)

(72) Inventors: Christopher W. Shade, Louisville, CO (US); Steven Tieu, Louisville, CO (US)

(73) Assignee: Quicksilver Scientific, Inc., Louisville, CO (US)

( * ) Notice: Subject to any disclaimer, the term of this patent is extended or adjusted under 35 U.S.C. 154(b) by 247 days.

(21) Appl. No.: 18/209,168

(22) Filed: Jun. 13, 2023

(65) Prior Publication Data

US 2023/0398164 A1 Dec. 14, 2023

Related U.S. Application Data

(60) Continuation-in-part of application No. 17/584,661, filed on Jan. 26, 2022, now Pat. No. 12,121,558, which is a division of application No. 16/849,654, filed on Apr. 15, 2020, now Pat. No. 11,291,702.

(60) Provisional application No. 62/834,013, filed on Apr. 15, 2019.

(51) Int. Cl.

| | |
|---|---|
| A61K 36/288 | (2006.01) |
| A61K 9/00 | (2006.01) |
| A61K 9/107 | (2006.01) |
| A61K 31/355 | (2006.01) |
| A61K 31/381 | (2006.01) |
| A61K 31/404 | (2006.01) |
| A61K 36/328 | (2006.01) |
| A61K 36/515 | (2006.01) |
| A61K 47/14 | (2017.01) |
| A61K 47/44 | (2017.01) |
| B82Y 5/00 | (2011.01) |

(52) U.S. Cl.
CPC .......... *A61K 36/288* (2013.01); *A61K 9/0053* (2013.01); *A61K 9/1075* (2013.01); *A61K 31/355* (2013.01); *A61K 31/381* (2013.01); *A61K 31/404* (2013.01); *A61K 36/328* (2013.01); *A61K 36/515* (2013.01); *A61K 47/14* (2013.01); *A61K 47/44* (2013.01); *B82Y 5/00* (2013.01)

(58) Field of Classification Search
CPC .. A61K 36/288; A61K 9/0053; A61K 9/1075; A61K 31/355; A61K 31/381; A61K 31/404; A61K 36/328; A61K 36/515; A61K 47/14; A61K 47/44; A61K 9/0056; A61K 31/352; A61K 9/006; A61K 9/1271; A61K 47/10; A61K 47/22; A61K 47/24; B82Y 5/00
See application file for complete search history.

(56) References Cited

U.S. PATENT DOCUMENTS

| | | |
|---|---|---|
| 5,238,683 A | 8/1993 | Crystal |
| 5,260,065 A | 11/1993 | Mathur et al. |
| 5,395,619 A | 3/1995 | Zalipsky et al. |
| 5,565,439 A | 10/1996 | Piazza et al. |
| 5,569,464 A | 10/1996 | Endo et al. |
| 5,711,965 A | 1/1998 | Ghyczy et al. |
| 5,817,695 A | 10/1998 | Pellico |
| 5,834,014 A | 11/1998 | Weiner et al. |
| 5,871,769 A | 2/1999 | Fleming et al. |
| 5,935,588 A | 8/1999 | Afriat et al. |
| 6,048,886 A | 4/2000 | Neigut |
| 6,143,786 A | 11/2000 | Gohman et al. |
| 6,159,500 A | 12/2000 | Demopoulos et al. |
| 6,180,662 B1 | 1/2001 | Lanzendorfer et al. |
| 6,204,248 B1 | 3/2001 | Demopoulos et al. |
| 6,218,436 B1 | 4/2001 | Howard et al. |
| 6,235,271 B1 | 5/2001 | Luther et al. |
| 6,245,797 B1 | 6/2001 | Winokur |
| 6,287,611 B1 | 9/2001 | Morello et al. |
| 6,319,517 B1 | 11/2001 | Cavallo et al. |
| 6,337,065 B1 | 1/2002 | Jacobson et al. |
| 6,358,516 B1 | 3/2002 | Harod |
| 6,492,410 B1 | 12/2002 | Leopold et al. |
| 6,534,540 B2 | 3/2003 | Kindness et al. |

(Continued)

FOREIGN PATENT DOCUMENTS

| | | |
|---|---|---|
| EP | 0834301 A1 | 4/1998 |
| JP | 2010235538 A | 10/2010 |

(Continued)

OTHER PUBLICATIONS

Amory, et al., "Oral Testosterone in Oil Plus Dutasteride in Men: A Pharmacokinetic Study", 0021-972X; The Journal of Clinical Endocrinology & Metabolism 90(5):2610-2617 Printed in U.S.A. Copyright 2005 by The Endocrine Society doi: 10.1210/jc.2004-1221, May 2005, 8 Pages.

Ansari, Mohammad Javed, et al., "Formulation, characterization, in vitro and in vivo evaluations of self-nanoemulsifying drug delivery system of luteolin", Mohammad Javed Ansari, et al., (2020) Formulation, characterization, invitro and invivo evaluations of self-nanoemulsifying drug delivery system of luteolin, Journal of Taibah University for Science, 14:1, 1386-1401, DOI: 10.1080/16583655. 2020.1812269, Sep. 26, 2020, 17 pages.

(Continued)

*Primary Examiner* — Snigdha Maewall
(74) *Attorney, Agent, or Firm* — Blanchard Horton PLLC

(57) ABSTRACT

An intra-oral, nanoemulsion assists in balancing the histamine response in subjects when orally administered. The intra-oral, nanoemulsion includes at least one monolayer surfactant bound particle and a continuous phase. The monolayer surfactant bound particles are carried by the continuous phase. A method of making and of administering the nanoemulsion to balance the histamine response in subjects also is described. The nanoemulsion is ingestible and edible.

25 Claims, 2 Drawing Sheets

(56)                References Cited

U.S. PATENT DOCUMENTS

| 6,562,369 | B2 | 5/2003 | Luo et al. |
| 6,596,305 | B1 | 7/2003 | Edgerly-Plug |
| 6,630,157 | B1 | 10/2003 | Horrobin et al. |
| 6,713,533 | B1 | 3/2004 | Panzner |
| 6,764,693 | B1 | 7/2004 | Smith |
| 7,825,084 | B2 | 11/2010 | Harris et al. |
| 8,067,381 | B1 | 11/2011 | Harris et al. |
| 8,114,913 | B1 | 2/2012 | Guilford et al. |
| 8,147,869 | B2 | 4/2012 | Guilford et al. |
| 8,252,325 | B2 | 8/2012 | Guilford et al. |
| 8,282,977 | B2 * | 10/2012 | Bromley ............ A61K 9/1075 |
| | | | 426/443 |
| 8,349,359 | B2 | 1/2013 | Guilford et al. |
| 8,679,530 | B2 | 3/2014 | Guilford et al. |
| 8,741,373 | B2 | 6/2014 | Bromley et al. |
| 9,474,725 | B1 | 10/2016 | Reillo et al. |
| 9,730,911 | B2 | 8/2017 | Verzura et al. |
| 9,839,612 | B2 | 12/2017 | Reillo et al. |
| 9,925,149 | B2 | 3/2018 | Kaufman |
| 9,972,680 | B2 | 5/2018 | Reillo et al. |
| 9,974,739 | B2 | 5/2018 | Reillo et al. |
| 10,016,389 | B2 | 7/2018 | Zhang |
| 10,084,044 | B2 | 9/2018 | Reillo et al. |
| 10,103,225 | B2 | 10/2018 | Reillo et al. |
| 10,239,808 | B1 | 3/2019 | Black et al. |
| 11,291,702 | B1 | 4/2022 | Shade et al. |
| 2002/0025313 | A1 | 2/2002 | Micklus et al. |
| 2002/0048551 | A1 | 4/2002 | Keller et al. |
| 2002/0102316 | A1 | 8/2002 | Weissman |
| 2002/0106339 | A1 | 8/2002 | Fisher et al. |
| 2002/0132781 | A1 | 9/2002 | Kindness et al. |
| 2002/0137785 | A1 | 9/2002 | Kindness et al. |
| 2002/0169195 | A1 | 11/2002 | Kindness et al. |
| 2002/0182585 | A1 | 12/2002 | Kindness et al. |
| 2002/0187130 | A1 | 12/2002 | Kindness et al. |
| 2003/0059462 | A1 | 3/2003 | Barenholz et al. |
| 2003/0083241 | A1 | 5/2003 | Young |
| 2003/0096000 | A1 | 5/2003 | Solis et al. |
| 2003/0157220 | A1 | 8/2003 | Morello et al. |
| 2003/0162829 | A1 | 8/2003 | Kindness et al. |
| 2004/0022841 | A1 | 2/2004 | Hassan et al. |
| 2004/0022873 | A1 | 2/2004 | Guilford et al. |
| 2004/0127476 | A1 | 7/2004 | Kershman et al. |
| 2004/0170560 | A1 | 9/2004 | Fossheim et al. |
| 2005/0131041 | A1 | 6/2005 | Salman et al. |
| 2005/0191343 | A1 | 9/2005 | Liang |
| 2006/0099244 | A1 | 5/2006 | Guilford |
| 2006/0106093 | A1 | 5/2006 | Rich et al. |
| 2007/0065456 | A1 | 3/2007 | Woods |
| 2008/0131496 | A1 | 6/2008 | Guilford |
| 2008/0207679 | A1 | 8/2008 | Berkowitz |
| 2009/0047340 | A1 | 2/2009 | Guilford |
| 2009/0068253 | A1 | 3/2009 | Guilford |
| 2009/0069279 | A1 | 3/2009 | Astruc et al. |
| 2010/0086573 | A1 | 4/2010 | Anderson |
| 2010/0166846 | A1 | 7/2010 | Guilford |
| 2010/0173882 | A1 | 7/2010 | Giliyar et al. |
| 2010/0233193 | A1 | 9/2010 | Guilford et al. |
| 2010/0233297 | A1 | 9/2010 | Guilford et al. |
| 2010/0291196 | A1 | 11/2010 | Guilford |
| 2010/0316700 | A1 | 12/2010 | Guilford |
| 2011/0020436 | A1 | 1/2011 | Guilford |
| 2011/0129523 | A1 | 6/2011 | Guilford et al. |
| 2011/0274625 | A1 | 11/2011 | Redelmeier et al. |
| 2011/0305752 | A1 | 12/2011 | Guilford et al. |
| 2012/0087994 | A1 | 4/2012 | Guilford et al. |
| 2012/0135068 | A1 | 5/2012 | Guilford et al. |
| 2012/0141608 | A1 | 6/2012 | Guilford et al. |
| 2012/0171280 | A1 | 7/2012 | Zhang |
| 2012/0219616 | A1 | 8/2012 | Guilford et al. |
| 2012/0225053 | A1 | 9/2012 | Dushenkov et al. |
| 2012/0282325 | A1 | 11/2012 | Tong et al. |
| 2013/0045271 | A1 | 2/2013 | Dadey et al. |
| 2013/0231297 | A1 | 9/2013 | Krawitz |
| 2014/0161784 | A1 | 6/2014 | Westerlund et al. |
| 2015/0079156 | A1 | 3/2015 | Kett et al. |
| 2015/0296856 | A1 | 10/2015 | Chandra et al. |
| 2016/0000710 | A1 * | 1/2016 | Gupta .................. A61K 31/352 |
| | | | 514/23 |
| 2016/0023826 | A1 | 1/2016 | Edwards et al. |
| 2016/0166516 | A1 | 6/2016 | Gannon et al. |
| 2016/0263047 | A1 | 9/2016 | Kaufman |
| 2017/0127712 | A1 | 5/2017 | Yiannios |
| 2018/0263283 | A1 | 9/2018 | Popplewell et al. |
| 2020/0170272 | A1 | 6/2020 | Bromley |

FOREIGN PATENT DOCUMENTS

| WO | 199111117 | A2 | 8/1992 |
| WO | 199855075 | A2 | 12/1998 |
| WO | 20010126618 | A2 | 4/2001 |
| WO | 2005041657 | A1 | 5/2005 |
| WO | 2006128032 | A2 | 11/2006 |
| WO | 2008100629 | A2 | 8/2008 |
| WO | 2012066334 | A1 | 5/2012 |
| WO | 2016020485 | A1 | 2/2016 |

OTHER PUBLICATIONS

Casson, et al., "Delivery of Dehydroepiandrosterone to Premenopausal Women: Effects of Micronization and Nonoral Administration", American Journal of Obstetrics and Gynecology, 174(2), Retrieved from :<<http://www. hormonebalance.org/images/documents/Casson%2096%20Vag%20vs%20oral%20DHEA%20AJOG. pdf>>, Feb. 1996, 4 Pages.

Dilova, et al., "Increasing the Solubility of a Poor Soluble Api— Milk Thistle Dry Extract (Silymarin)", Pharmacia, 61(1), 2014, 18-21.

Farina, et al., "Metals, Oxidative Stress and Neurodegeneration: A Focus on Iron, Manganese and Mercury", NIH Public Access, Neurochem Int., 62(5), Apr. 2013, 575-594.

Hazekamp, Arno, "The Trouble with CBD Oil", Hazekamp Herbal Consulting, Leiden, The Netherlands; Med Cannabis Cannabinoids 2018;1:65-72; DOI: 10.1159/000489287, Jun. 12, 2018, 8 Pages.

Hsu, et al., "Use of Lipid Nanocarriers to Improve Oral Delivery of Vitamins", Nutrients 2019, 11, 68; doi:10.3390/nu11010068 www. mdpi.com/journal/nutrients, 2019.

Kale, et al., "Emulsion Micro Emulsion and Nano Emulsion: A Review", Sys Rev Pharm, 8(1), 2017, 39-47.

Mlcek, Jiri, et al., "Quercetin and Its Anti-Allergic Immune Response", Mlcek, et al. "Quercetin and Its Anti-Allergic Immune Response," Molecules 2016, 21, 623; doi:10:3390, pp. 1-15, 2016, 15 pages.

Shaik, Yasdani, et al., "Impact of polyphenols on mast cells with special emphasis on the effect of quercetin and luteolin", Shaik, et al. "Impact of polyphenols on mast cells with special emphasis on the effect of quercetin and luteolin," Central EU Journal of Immunology 2018; 43(4), pp. 476-481, 2018, 6 pages.

Tan, et al., "Tocotrienols Vitamin E Beyond Tocopherols", CRC Press, Second Edition, Sec. 2.3, Nov. 16, 2016, 2 Pages.

Thangam, Elden Berla, et al., "The Role of Histamine and Histamine Receptors in Mast Cell-Mediated Allergy and Inflammation: The Hunt for New Therapeutic Targets", Thangam EB, et al. (2018) The Role of Histamine and Histamine Receptors in Mast Cell-Mediated Allergy and Inflammation: The Hunt for New Therapeutic Targets. Front. Immunol. 9:1873. doi: 10.3389/fimmu.2018.01873, Aug. 2018, 9 pages.

Wu, Kai Connie, et al., "Effect of Graded Nrf2 Activation on Phase-1 and -11 Drug Metabolizing Enzymes and Transporters in Mouse Liver", Wu KC, Cui JY, Klaassen CD (2012) Effect of Graded Nrf2 Activation on Phase-I and -II Drug Metabolizing Enzymes and Transporters in Mouse Liver. PLoS ONE 7(7): e39006. doi:10.1371/journal.pone.0039006, Jul. 2012, 10 pages.

* cited by examiner

INTRA-ORAL NANOEMULSION INCLUDING MONOLAYER SURFACTANT BOUND PARTICLES FOR BALANCING HISTAMINE RESPONSE

REFERENCE TO RELATED APPLICATIONS

This application is a continuation-in-part of U.S. Non-provisional application Ser. No. 17/584,661, filed Jan. 26, 2022, entitled "Liver Activation Nanoemulsion, Solid Binding Composition, and Toxin Excretion Enhancement" which is a division of U.S. Nonprovisional application Ser. No. 16/849,654, filed Apr. 15, 2020, entitled "Liver Activation Nanoemulsion, Solid Binding Composition, and Toxin Excretion Enhancement Method", which claims the benefit of U.S. Provisional Application No. 62/834,013 entitled "Liver Activation Nanoemulsion, Solid Binding Composition, and Toxin Excretion Enhancement Method" filed Apr. 15, 2019, all of which are incorporated by reference in the entirety, except that in the event of any inconsistent disclosure or definition from the present application, the disclosure or definition herein shall prevail.

BACKGROUND

Histamine and its receptors in the body play a significant role in allergic response. Four histamine receptors (H1R-H4R) are known to be expressed on different cell types. Histamine is involved in the regulation of many body processes including the secretion of gastric acid, inflammation, vasodilation, bronchoconstriction, and potentially as a neurotransmitter.

Mast cells are the major producers of histamine in the body as the mast cells contain and release several inflammatory compounds and are essential for allergies, innate and acquired immunity, and inflammation. The mast cells mediate these processes through the release of various mediators and produce leukotrienes.

Activated mast cells generate cytokines/chemokines which together with neuropeptides underlie several neuropathological processes and are believed to contribute to central nervous system inflammation. This inflammation causes sensory nerves to release neuropeptides that cause an increase in vascular permeability, plasma extravasation, and edema. Mast cells may be activated to release histamine by cytokines, growth factors, hormones, and bacterial and viral infection. Thus, while mast cell activation is part of the desired immune response to bacterial and viral infection, such activation can occur when it is not necessary to protect the body and once started can continue without need. The unnecessary or excessive release of histamine by the mast cells is believed to be associated with brain fog, itchy eyes, fatigue, and undesirable immune response including runny nose and redness of the face. When severe, overactive mast cells can result in a condition referred to as Mast Cell Activation Syndrome (MCAS).

Substances that are toxic to humans are continually introduced to the body from the environment, and when toxin intake exceeds removal rate, toxins accumulate in the body. The liver, associated gall bladder, and bowel are organs substantially involved in removing toxins. However, in serving their role as toxin eliminators, over time toxins build up in these organs that are either poorly or not eliminated. Thus, while the body may effectively transfer toxins to these organs for excretion and elimination, some types of toxins are poorly excreted and/or eliminated. Such poor excretion/elimination of toxins over time can result in an increasing habitual toxin concentration in the body, increased base inflammation throughout the body, and a potential increase in unwanted mast cell activity and resultant histamine release in response to the elevated habitual toxin concentration induced inflammation.

FIG. 1 represents a micelle 100 having a single wall of phospholipids (monolayer) forming a hydrophilic exterior 120 and a hydrophobic interior 110 lacking the hydrophilic capsule interior of a liposome. Thus, in relation to a liposome, a micelle lacks a bilayer and does not provide the capsule interior that can contain a water-soluble, hydrophilic core composition. The micelle 300 may be thought of as the outer wall of a liposome without the inner wall providing for a capsule interior. Polyethylene glycol modified vitamin E, such as tocopheryl polyethylene glycol succinate 1000 (TPGS), may be used to form micelles in water as the TPGS has a water-soluble head and an oil-soluble tail. While not shown in the figure, a reverse micelle is formed in a nonpolar as opposed to the "normal" polar continuous phase, which results in the normally hydrophobic interior of the micelle being reversed and the "reverse micelle" having a hydrophilic interior.

FIG. 2 represents a monolayer surfactant where the oil component is associated with the hydrophobic tails of a surfactant. In this representation, the surfactant has formed a circular shape, thus encircling the oil component and approximating a relatively large, expanded micelle, but such encircling is not required for the oil component to associate with the hydrophobic tails.

Diindolylmethane (DIM) is a compound derived from indole-3-carbinol which is found in cruciferous vegetables such as broccoli, brussels sprouts, cabbage and kale. DIM is reported to induce the antioxidant response element (ARE) and to support healthy estrogen levels when used as a nutritional supplement; however, is also known to have poor oral bioavailability.

Quercetin is a plant polyphenol from the flavonoid group, found in many fruits, vegetables, leaves, and grains. When IV administered, quercetin acts as an antioxidant by scavenging (deactivating) free radicals, such as oxygen radicals, and as an activator of estrogen receptors. Quercetin is recognized as an anti-inflammatory and to inhibit histamine release. However, the bioavailability of quercetin in humans is low and highly variable (0-50%), and is rapidly cleared with an elimination half-life of 1-2 hours after oral ingestion of quercetin containing foods or supplements. Following dietary ingestion, quercetin undergoes rapid and extensive metabolism that makes the biological effects observed in IV administered studies unlikely to apply to conventional oral administration.

Luteolin is a flavone found in celery, broccoli, green pepper, parsley, thyme, dandelion, perilla, chamomile tea, carrots, olive oil, peppermint, rosemary, navel oranges, and oregano. Plants rich in luteolin have been used in Chinese traditional medicine and as a nutritional supplement for treating various diseases such as hypertension, inflammatory disorders, and cancer. However, the oral bioavailability of luteolin in rats is reported to be <30% due to the low solubility in water. Poorly water-soluble deliverables often have low or erratic absorption resulting in low oral bioavailability with high uptake variability.

Nutritional supplements are conventionally introduced to the bloodstream in multiple ways. Supplements taken orally are absorbed at different rates due to different factors. For example, on average about 10% to 20% of a solid supplement taken orally is absorbed. This can be increased to about 30% with an orally taken gel capsule, to about 45% with a transdermal patch, and to about 50% with conventional intra-oral (sublingual) administration. Injections provide from approximately 90% to 100% adsorption into the blood-stream, but are uncommonly used for nutritional supplements.

The present invention avoids or ameliorates at least some of the disadvantages of conventional oral supplement preparations intended to affect histamine response in a subject.

SUMMARY

In one aspect of the invention, there is an intra-oral nanoemulsion for balancing the histamine response a subject when intra-orally administered, the nanoemulsion includes at least one monolayer surfactant bound particle, where the at least one monolayer surfactant bound particle includes at least one amphiphilic fat, a polyethylene glycol surfactant, an associating oil, diindolylmethane, quercetin, and luteolin; and a continuous phase including glycerin, ethanol, and water; where the nanoemulsion is a stable dispersion that is transparent, and the at least one monolayer surfactant bound particle has an average particle diameter from 10 to 100 nanometers as carried by the continuous phase.

In another aspect of the invention, there is a method of balancing histamine response in a subject, the method includes holding from 4 to 6 milliliters of a nanoemulsion under the tongue of an animal from 30 seconds to 2 minutes, where the nanoemulsion includes at least one monolayer surfactant bound particle, where the at least one monolayer surfactant bound particle includes at least one amphiphilic fat, a polyethylene glycol surfactant, an associating oil, diindolylmethane, quercetin, and luteolin; and a continuous phase including glycerin, ethanol, and water; where the nanoemulsion is a stable dispersion that is transparent, and the at least one monolayer surfactant bound particle has an average particle diameter from 10 to 100 nanometers as carried by the continuous phase.

In another aspect of the invention, there is a method of making an intra-oral nanoemulsion for balancing histamine response in subjects when orally administered, the method includes forming a mixture including an amphiphilic fat including at least 30% by weight phosphatidylcholine, a polyethylene glycol surfactant, an associating oil, diindolyl-methane, quercetin, luteolin, glycerin, ethanol, and water to form a nanoemulsion; and stirring the nanoemulsion at room temperature and pressure to form a stable dispersion that is transparent and has an average particle diameter from 10 to 100 nanometers.

Other systems, methods, features, and advantages of the invention will be, or will become, apparent to one with skill in the art upon examination of the following figures and detailed description. It is intended that all such additional systems, methods, features, and advantages be included within this description, be within the scope of the invention, and be protected by the claims that follow. The scope of the present invention is defined solely by the appended claims and is not affected by the statements within this summary.

BRIEF DESCRIPTION OF THE FIGURES

The invention can be better understood with reference to the following drawings and description. The components in the figures are not necessarily to scale and are not intended to accurately represent molecules, emphasis instead being placed upon illustrating the principles of the invention.

DETAILED DESCRIPTION

Figure 1:
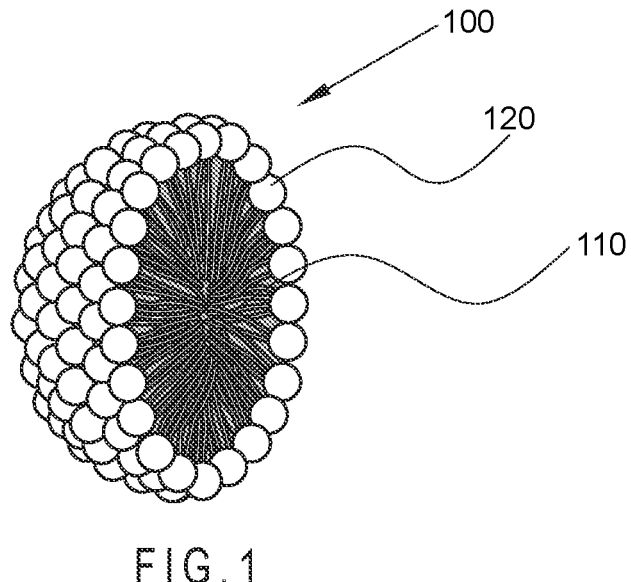
FIG. 1 represents a micelle having a single wall of phospholipids (monolayer) forming a hydrophilic exterior and a hydrophobic interior lacking the capsule interior of a liposome.
Figure 2:
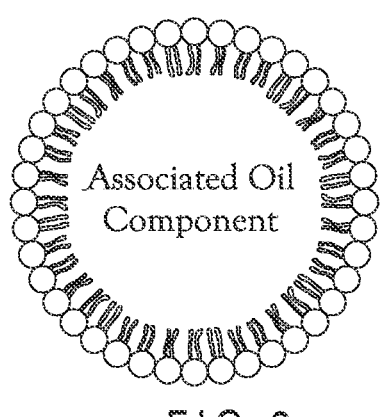
FIG. 2 represents a monolayer surfactant where the oil component is associated with the hydrophobic tails of the surfactant.

An intra-oral, nanoemulsion assists in balancing the histamine response in subjects when orally administered. The intra-oral, nanoemulsion includes at least one monolayer surfactant bound particle and a continuous phase. The monolayer surfactant bound particles are carried by the continuous phase. A method of making and of administering the nanoemulsion to balance the histamine response in subjects also is described. The nanoemulsion is ingestible and edible.

Pharmaceuticals exist that can selectively target and thus block one or more of the different histamine receptors; however, unless a histamine related, fairly severe disease state exists, such pharmaceuticals are not warranted or may not be desired due to their associated side effects. Side effects of such pharmaceuticals can include dry mouth, drowsiness, dizziness, an inability to evacuate the bladder, and restlessness or moodiness in some children. However, it is believed that balancing the histamine response at least in part through a reduction in histamine release and separately but concurrently through a reduction in histamine induced inflammation could be advantageous in some circumstances without the associated unwanted side effects of pharmaceutical histamine blockers.

For example, luteolin is believed to inhibit the release of histamines from mast cells, as opposed to binding previously produced histamines or blocking histamine receptors. DIM is believed to regulate the T-cell response to cytokines, possibly lower reactive cytokine levels, and reduce the secondary inflammation attributed to histamine overproduction. Quercetin is believed to provide the added benefit of mold detoxification, thus reducing the habitual toxin concentration, its associated inflammation, and the unwanted release of histamines by the mast cells in response to the inflammation. Thus, luteolin, DIM, and quercetin are believed to function in a way that is different from conventional histamine binders and receptor blockers. The combination of luteolin, DIM, and quercetin in the appropriate ratios is believed to synergistically balance the histamine response by reducing histamine release while concurrently reducing unwanted inflammation.

The nanoemulsion is an oil-in-water dispersion including the at least one monolayer surfactant bound particle where the oil of the particle is associated with a surfactant system. The at least one monolayer surfactant bound particle includes diindolylmethane, quercetin, and luteolin in a ratio of 0.5:0.8:1±20%.

The oil of the at least one monolayer surfactant bound particle includes an associating oil selected from the group consisting essentially of medium chain triglycerides (MCT), citrus oil, and combinations thereof. The oil of the monolayer surfactant bound particle includes diindolylmethane (DIM), quercetin, and luteolin, thus alcohol-soluble deliverables. While these deliverables have solubility in MCT oils and thus are "oil-soluble deliverables" at one level, they have greater solubility in ethanol and thus are considered alcohol-soluble deliverables. An oil-soluble tocopherol or tocotrienol (Vitamin E form) is preferably also included in the oil of the monolayer surfactant bound particles. Being oil-soluble deliverables, the tocopherol and tocotrienol are more soluble in oil than in ethanol.

The surfactant system of the monolayer surfactant bound particle includes phosphatidylcholine (PC) and tocopheryl polyethylene glycol succinate (TPGS) surfactants. The ratio of PC to TPGS is from 1:1.8 to 1:3 by weight in the surfactant system of the monolayer surfactant bound particle. Preferably, the at least one monolayer surfactant bound particle surfactant system has a PC to TPGS ratio from 1:1.6 to 1:3 by weight.

The monolayer surfactant bound particles have an average diameter from 10 to 125 nanometers (nm) or from 10 to 100 nm, preferably from 10 to 80 nm, and more preferably from 10 to 60 nm. The approximately 125-nm average diameter upper limit is important, as particles larger than this will not transport effectively through the tissues of the mouth and enter the bloodstream, but instead will enter the stomach and be substantially irreversibly chemically altered (digested), and thus deactivated, by acid and bile salts.

The 100 nm average diameter upper limit of the monolayer surfactant bound particles provides transparency to the nanoemulsion, as larger average particle diameters provide translucent liquids that degrade into milky liquids if unstable. Thus, average particle diameters of 100 nm and less are preferred to provide a nanoemulsion that is transparent with optimized intra-oral delivery.

The continuous phase of the nanoemulsion includes water, glycerin, and ethanol. Vitamin C is preferably included in the continuous phase. The continuous phase of the nanoemulsion constitutes from 70% to 90% by weight of the nanoemulsion, with the remaining nanoemulsion weight attributable to the monolayer surfactant bound particles, supplement constituents including the alcohol- and oil-soluble supplement constituents, and the like.

The continuous phase of the nanoemulsion preferably constitutes about 70% by weight of the nanoemulsion, and the ratio of glycerin to ethanol to water is approximately 1.3:1:1.4 with deviations of ±30% or ±20%. The nanoemulsion is at least 20% glycerin by weight and at least 20% ethanol by weight. The nanoemulsion is at least 25% water by weight, preferably at least 30% by weight. The continuous phase of the nanoemulsion lacks sufficient relatively nonpolar glycerin to form an "invert" or "water-in-oil" emulsion.

The ethanol is preferably USP food grade 190 proof (95% ethanol, 5% water). If the ethanol includes more than 10% water, the additional water should be considered in relation to the total water content of the nanoemulsion to prevent precipitation of the alcohol- and/or oil-soluble deliverables.

To achieve the desired ratios of the histamine balancing supplement constituents at the cellular level, the transport of the supplement constituents should be controlled from introduction to the body until the supplement constituents reach the immune cells. Without the nanoemulsion, the body will alter the concentration and ratios of the supplement constituents inconsistently with each introduction. However, as the nanoemulsion substantially avoids digestion by the stomach, liver and intestine, the delivered alcohol- and oil-soluble supplement constituents enter the bloodstream substantially unaltered. Thus, intra-oral delivery of the nanoemulsion including the monolayer surfactant bound particles carried by the continuous phase prevents the extensive metabolism of the alcohol- and oil-soluble supplement constituents observed for conventional, orally-administered supplements whose primary absorption path is through the gut.

Thus, it is believed that the nanoemulsion allows the luteolin, DIM, quercetin, and optional tocopherol and/or tocotrienol to be transported to the cells substantially simultaneously and in the desired ratios to maximize histamine response balancing. Furthermore, the monolayer surfactant bound particles are believed to allow the alcohol- and optional oil-soluble deliverables to reach the bloodstream at a rate substantially like that of any water-soluble continuous phase deliverables present in the nanoemulsion, such as the water-soluble Vitamin C.

Furthermore, without the combination of the monolayer surfactant bound particle to carry the alcohol- and oil-soluble deliverables in combination with the constituents and constituent ratios of the continuous phase, the blood delivery performance, transparency, and stable dispersion of the nanoemulsion could not be achieved.

In addition to maintaining the supplement constituent ratios at the cellular level for histamine balancing, without initially passing through the gut, the nanoemulsion provides substantially enhanced bioavailability for the alcohol- and oil-soluble supplement constituents in relation to conventional, orally-administered supplements. In fact, it is believed that the monolayer surfactant bound particles of the nanoemulsion can approach IV administration in the rate and concentrations at which the body transfers the alcohol- and oil-soluble supplement constituents of the nanoemulsion into the bloodstream.

In addition to the advantage of not requiring venipuncture for relatively rapid and high bloodstream concentration bioavailability of the alcohol- and oil-soluble deliverables, especially in comparison to conventional, orally-administered supplements, the nanoemulsion is believed to maintain a longer-duration increased concentration of the delivered alcohol- and oil-soluble supplement constituents in the bloodstream than available from IV injection, and thus a longer duration, high-concentration availability to the living cells.

Other constituents, such as flavorings, sodium hydroxide (NaOH), non-tocopherol or tocotrienol forms of Vitamin E, and acacia gum may be included in the nanoemulsion. The other constituents are selected to not interfere with the beneficial operation of the histamine balancing supplement constituents and the physical structure of the nanoemulsion providing the enhanced delivery and deliverable solubility in relation to conventional systems.

The following examples illustrate one or more preferred embodiments of the invention. Numerous variations may be made to the following examples that lie within the scope of the invention.

EXAMPLES

Example 1: Constituents of the Intra-Oral, Nanoemulsion

A nanoemulsion was prepared having a 5 mL total volume. The nanoemulsion included approximately 20 mg of DIM, approximately 10 mg of anhydrous quercetin, and approximately 10 mg of luteolin extract by weight. The nanoemulsion also included approximately 100 to 200 mg of PC, approximately 700 to 1300 mg ethanol, approximately 1000 to 1600 mg glycerin, and minor amounts of flavoring as an other constituent. TPGS was included to provide the desired physical structures in the nanoemulsion. In addition to these ingredients, the nanoemulsion included enough water to provide a total volume of 5 mL. Vitamin C was included in the continuous phase.

Example 2: A Method of Making an Intra-Oral, Nanoemulsion

The monolayer surfactant bound particle of the nanoemulsion was made by combining approximately 4 mg DIM, 3 mg quercetin anhydrous, and 3 mg luteolin extract in associating oil and ethanol. The combination was then combined with PC, TPGS, glycerin, and water. The combination was then mixed to form a first emulsion.

To the first emulsion was added approximately 4 mg of ethanol and approximately 8 mg of glycerin. This combination was then mixed to form a second emulsion.

The total volume of the second emulsion was then increased to approximately 5 mL with water including the optional Vitamin C. Mixing was performed in a mechanically stirred vessel.

Example 3: Histamine Response Balancing

A. Human subjects were selected that were believed to have allergy-induced nasal congestion. On an empty stomach, the human subjects placed 5 mL of the nanoemulsion under the tongue. The nanoemulsion was held under the tongue for approximately 30 seconds to 2 minutes before swallowing. The subjects then consumed approximately 250 mL of water. After approximately 10 minutes the subjects reported a drying of the nose and throat and an enhanced ability to effortlessly breath attributable to a more "open" feeling in the sinuses.

B. A human male subject was selected that demonstrated facial redness under the eyes continuing up and around the eyes into the forehead after alcohol consumption. This redness was believed attributable to unnecessary mast cell activation.

On an empty stomach, the human subject placed 5 mL of the nanoemulsion under the tongue. The nanoemulsion was held under the tongue for approximately 30 seconds to 2 minutes before swallowing. The subject then consumed approximately 250 mL of water. After approximately 10 minutes the redness in the subject's face had nearly disappeared, and the subject reported that his face no longer felt "hot".

C. A human male subject was selected that was experiencing swelling of the throat in response to seafood. This swelling was believed attributable to unnecessary mast cell activation in view of an allergic response.

On an empty stomach, the human subject placed 2 mL of the nanoemulsion under the tongue. The nanoemulsion was held under the tongue for approximately 30 seconds to 2 minutes before swallowing. The subject then consumed approximately 250 mL of water. After approximately 4 to 5 minutes the subject reported a reduction in the swelling.

Example 4: Bioavailability Uptake and Duration for a Water-Soluble Vitamin with a Liposomal Nanoemulsion On an empty stomach, a human subject placed 5 mL of a nanoemulsion including a water-soluble vitamin under the tongue. The nanoemulsion included a bilayer liposome including PC and TPGS including the water-soluble vitamin and a continuous phase. While not identical to the nanoemulsion providing histamine response balancing, it is believed that the bioavailability of the alcohol- and optional oil-soluble components via the previously discussed monolayer surfactant bound particle and continuous phase would be comparable to the bioavailability provided by the bilayer liposome to the water-soluble vitamin.

The nanoemulsion was held under the tongue for approximately 30 seconds to 2 minutes before swallowing. Blood samples were collected before the nanoemulsion was administered and at varying time intervals between 5 and 50 minutes after administration of the nanoemulsion for approximately 4 hours. This procedure was repeated for the water-soluble vitamin in approximately 5 mL of water and for the water-soluble vitamin in a conventional amphiphilic fat-based liposome lacking TPGS. The collected blood samples were analyzed for the concentration of the water-soluble vitamin.

Figure 3:
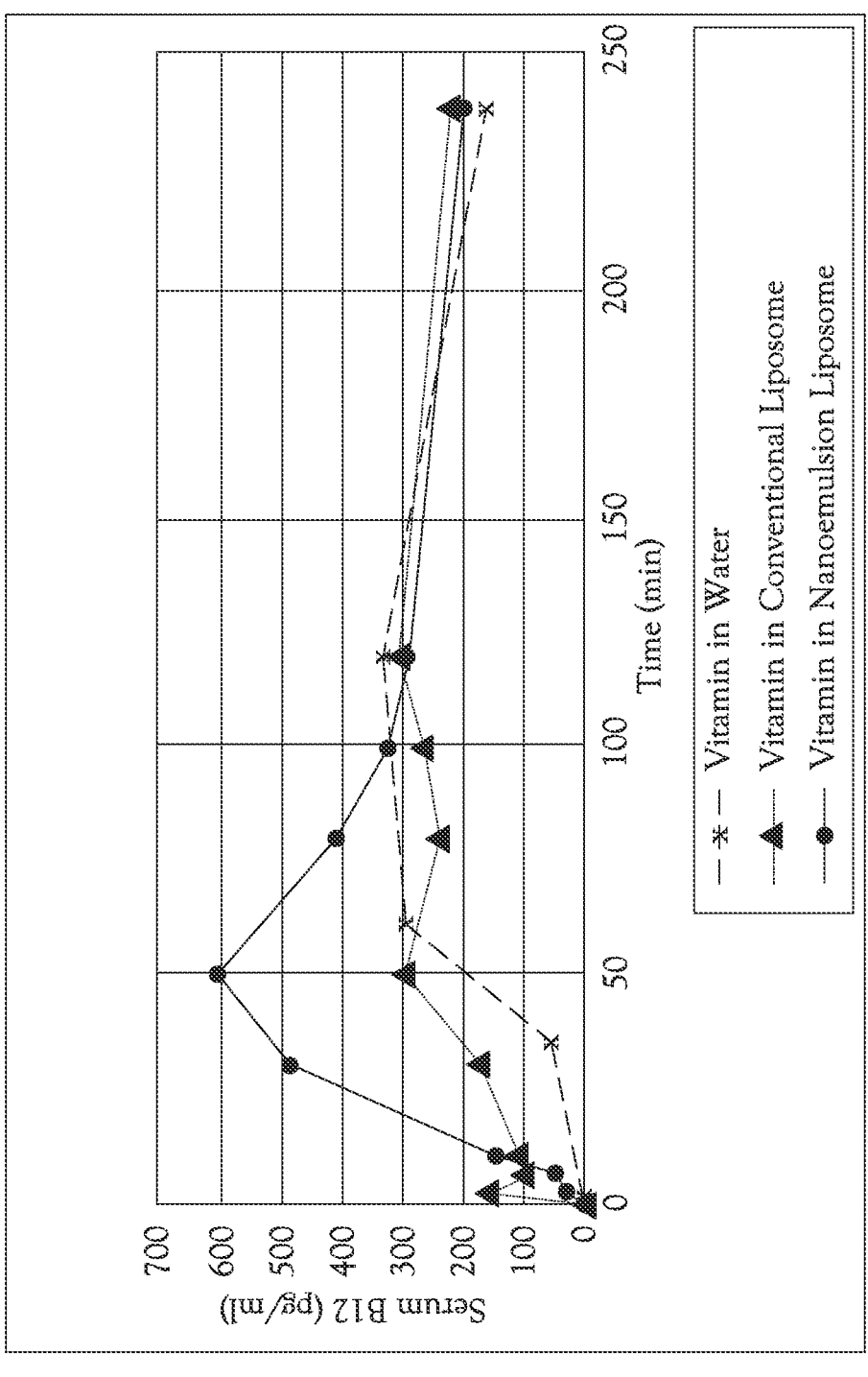
FIG. 3 provides the results of a bioavailability duration analysis in graphical form.

FIG. 3 provides the results of the bioavailability uptake and duration analysis in graphical form. The comparative data establishes that the nanoemulsion administration provides an approximate doubling of the blood concentration of the water-soluble vitamin 50-minutes post administration in relation to the water and conventional amphiphilic fat-based liposome administered vitamin. In addition to the initial and rapid uptake doubling, the blood concentration of the water-soluble vitamin provided by the nanoemulsion remains substantially above the water and conventional amphiphilic fat-based liposome administered blood concentrations until approximately 100-minutes post administration. Thus, establishing the ability of the nanoemulsion to provide supplement constitute blood concentrations approaching 100% greater than those provided by conventional oral administration methods.

Prophetic Example 1: Delivery Profile of Alcohol- and Oil-Soluble Monolayer Surfactant Bound Particle Deliverables Preferably, 4 to 6 mL of the nanoemulsion held under the tongue from 30 seconds to 2 minutes provides an at least 400 picograms per milliliter (pg/mL) concentration of the alcohol- and optional oil-soluble monolayer surfactant bound particle deliverables in the blood within 40 to 60 minutes of administration to subjects weighing from 50 kg to 90 kg. More preferably, 4 to 6 mL of the nanoemulsion held under the tongue from 30 seconds to 2 minutes provides an at least 500 pg/mL concentration of the monolayer surfactant bound particle deliverables in the blood within 40 to 60 minutes of administration to subjects weighing from 50 kg to 90 kg. This delivery profile is believed obtainable based on that observed for the water-soluble vitamin liposomal delivery nanoemulsion.

To provide a clear and more consistent understanding of the specification and claims of this application, the following definitions are provided.

Intra-oral delivery means that at least 40%, preferably 60%, and more preferably 80% and above of the delivery into the bloodstream that occurs upon oral administration of the liquid including the deliverable occurs by transmucosal absorption through the mouth, throat and esophagus before the liquid reaches the stomach. For particles to be considered suitable for intra-oral delivery, the average particle diameter is at most 125 nm and preferably less than 80 nm. For example, particles having an average diameter of 100 would have only an approximately 40% delivery to the bloodstream intra-orally, while particles having an average diameter of 75 nm would have and approximate 60% intra-oral delivery to the bloodstream. An 80% or greater intra-oral delivery to the bloodstream may be achieved with an average particle diameter of approximately 50 nm in 0.5 mL liquid after a mouth-residency time of 2 minutes.

Solutions lack an identifiable interface between the solubilized molecules and the solvent. In solutions, the solubilized molecules are in direct contact with the solvent.

Liquids are substances that are not a solid or a gas at room temperature and pressure. A liquid is an incompressible substance that flows to take on the shape of its container.

Emulsions are mixtures of two or more liquids that do not solubilize. Thus, one of the liquids carries isolated particles in the form of droplets of the other liquid. The particles of one liquid may be said to be dispersed in the continuous phase of the other liquid. An interface, separation, or boundary layer exists between the two liquids, thus between the continuous phase and the particles. Emulsions may be macroemulsions, pseudo-emulsions, microemulsions, or nanoemulsions. The primary difference between the types of emulsions is the size (average diameter) of the particles dispersed in the continuous phase and whether the particles are thermodynamically stable in the continuous phase. Macroemulsions and pseudo-emulsions have average particle diameters from 1 to 20 micrometers. Microemulsions and nanoemulsions have smaller average particle diameters in the continuous phase than macroemulsions and pseudo-emulsions. Microemulsions are thermodynamically stable while nanoemulsions are not, even though their average particle diameters may overlap in size.

A stable dispersion may be determined in one of two ways. One way to establish that a dispersion stored in a sealed container substantially excluding air and moisture is stable is when the oil phase particles in a continuous phase do not change in average diameter by more than +/−20% at about 25° C. for a time period of 3 months to 3 years, preferably for a time period of 6 months to 3 years, and more preferably, for a time period of 1 year to 3 years. Another way to establish that a dispersion is stable is when the oil phase particles in the continuous phase do not separate into a visibly distinct phase with a visible meniscus when stored in a sealed container substantially excluding air and moisture at about 25° C. for a time of 6 months to 3 years, and more preferably, for a time of 1 year to 3 years. A dispersion is stable if it meets either or both of these criteria.

Average particle diameter is determined by dynamic light scattering (DLS), sometimes referred to as photon correlation spectroscopy. The determination is made between 20° and 25° Celsius. One example of an instrument suitable for average particle diameter determination is a Nicomp 380 ZLS particle sizer as available from Particle Sizing Systems, Port Richey, FL. DLS can determine the diameter of particles in a liquid by measuring the intensity of light scattered from the particles to a detector over time. As the particles move due to Brownian motion the light scattered from two or more particles constructively or destructively interferes at the detector. By calculating the autocorrelation function of the light intensity and assuming a particle distribution, it is possible to determine the sizes of particles from 1 nanometer (nm) to 5 micrometers (um). The instrument is also capable of measuring the Zeta potential of particles.

Solid means a substance that is not a liquid or a gas. A solid substance may have one of a variety of forms, including a monolithic solid, a powder, a gel, or a paste.

Phosphatidylcholine (PC) molecules are a subset of the larger set of phospholipids and are commonly used to form liposomes in water. When placed in water without other constituents, the PC forms liposomes. The application of sufficient shear forces to the PC liposomes can reduce the bilayer liposome structures to monolayer structures, including micelles. PC has a head that is water-soluble and a tail that is much less water-soluble in relation to the head. PC is a neutral lipid, but carries an electric dipole moment of about 10 D between the head and the tail, making the molecule itself polar. While "PC" is used throughout this document for convenience, PC may be substituted with or combined with other amphiphilic fats. Preferable amphiphilic fats are isolated from lecithin. As the amphiphilic fat is preferably a phospholipid isolated from lecithin, the named isolates preferably include 80% (w/w) of the specified phospholipid with the remaining constituents being one or more additional phospholipids isolated from the lecithin or other lecithin isolates. Preferred phospholipid lecithin isolates include phosphatidylcholine (PC), phosphatidylethanolamine (PE), phosphatidylinositol (PI), ceramide phosphoryl ethanolamine (Cer-PE), ceramide phosphoryl choline (SPH), and combinations thereof, with PC, PE, and combinations thereof being more preferred. However, all phospholipid lecithin isolates are unexpectedly not interchangeable in forming the nanoemulsion as a stable dispersion that is also transparent. In fact, the phosphatidylserine (PS) and phosphatic acid (PA) isolates are not useful when a nanoemulsion that is a stable dispersion and is transparent is desired.

Tocopheryl polyethylene glycol succinate 1000 (TPGS) is generally considered a surfactant having a non-polar, oil-soluble "Vitamin E" tail and a polar, water-soluble polyethylene glycol head. While "TPGS" is used throughout this document for convenience, TPGS may be substituted with or combined with other polyethylene glycol surfactants including polysorbate 40, 60, or 80, preferably polysorbate 60 or 80.

Ingestible means capable of being ingested through the mouth by a living mammal while edible means fit to be eaten, thus in contrast to being unpalatable or poisonous. Edible also means that the composition has less than the permitted amount of viable aerobic microorganisms and meets the American Herbal Products Association (AHPA) guidelines for metals, adulterants, toxins, residual solvents, and pesticides.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless otherwise indicated, all numbers expressing quantities of ingredients, ratios, and the like used in the specification and claims are to be understood as indicating both the exact values as shown and as being modified by the term "about". Thus, unless indicated to the contrary, the numerical values of the specification and claims are approximations that may vary depending on the desired properties sought to be obtained and the margin of error in determining the values. At the very least, and not as an attempt to limit the application of the doctrine of equivalents to the scope of the claims, each numerical parameter should at least be construed considering the margin of error, the number of reported significant digits, and by applying ordinary rounding techniques.

The term "subject" refers to an animal, including, but not limited to, a primate (e.g., human, monkey, chimpanzee, gorilla, and the like), rodents (e.g., rats, mice, gerbils, hamsters, ferrets, and the like), lagomorphs, swine (e.g., pig, miniature pig), equine, canine, feline, and the like.

While various aspects of the invention are described, it will be apparent to those of ordinary skill in the art that other embodiments and implementations are possible within the scope of the invention. Accordingly, the invention is not to be restricted except considering the attached claims and their equivalents.

The invention claimed is:

1. An intra-oral nanoemulsion for balancing the histamine response in a subject when intra-orally administered, the nanoemulsion comprising:
  at least one monolayer surfactant bound particle, where
    the at least one monolayer surfactant bound particle comprises at least one amphiphilic fat, a polyethylene glycol surfactant, an associating oil, diindolylmethane, quercetin, and luteolin, where the diindolylmethane, the quercetin, and the luteolin are solubilized in the at least one monolayer surfactant bound particle; and
  a continuous phase comprising glycerin, ethanol, and water;
  where
    the at least one monolayer surfactant bound particle has a ratio of the amphiphilic fat to the polyethylene glycol surfactant from 1:1.8 to 1:3 by weight,
    the at least one amphiphilic fat is chosen from phosphatidylcholine (PC), phosphatidylethanolamine (PE), phosphatidylinositol (PI), ceramide phosphoryl ethanolamine (Cer-PE), ceramide phosphoryl choline (SPH), and combinations thereof,
    the polyethylene glycol surfactant is chosen from TPGS, polysorbate 80, polysorbate 60, and combinations thereof,
    the associating oil is chosen from medium chain triglycerides (MCT), citrus oil, and combinations thereof,
    the nanoemulsion is a stable dispersion that is transparent, and
    the at least one monolayer surfactant bound particle has an average particle diameter from 10 to 100 nanometers as carried by the continuous phase.

2. The nanoemulsion of claim 1, where the at least one monolayer surfactant bound particle further comprises at least one tocopherol or tocotrienol form of Vitamin E.

3. The nanoemulsion of claim 1, where the at least one amphiphilic fat is chosen from phospholipid lecithin isolates.

4. The nanoemulsion of claim 1, where the at least one amphiphilic fat comprises at least 30% phosphatidylcholine by weight.

5. The nanoemulsion of claim 1, where the polyethylene glycol surfactant comprises TPGS.

6. The nanoemulsion of claim 1, where a ratio of the diindolylmethane to the quercetin to the luteolin in the at least one monolayer surfactant bound particle is 0.5:0.8:1 ±20%.

7. The nanoemulsion of claim 1, where the nanoemulsion is ingestible and edible.

8. The nanoemulsion of claim 1, where the at least one monolayer surfactant bound particle has an average diameter from 10 to 60 nanometers.

9. The nanoemulsion of claim 1, where the ratio of the glycerin to the ethanol to the water in the continuous phase is 1.3:1:1.4 ±30% by weight.

10. The nanoemulsion of claim 1, where the continuous phase constitutes from 70% to 90% by weight of the nanoemulsion.

11. The nanoemulsion of claim 1 where the ratio of the amphiphilic fat to the polyethylene glycol surfactant ratio is from 1:1.6 to 1:3 by weight.

12. A method of balancing histamine response in a subject, the method comprising:
  holding from 4 to 6 milliliters of a nanoemulsion under the tongue of a subject from 30 seconds to 2 minutes, where the nanoemulsion comprises
  at least one monolayer surfactant bound particle, where
    the at least one monolayer surfactant bound particle comprises at least one amphiphilic fat, a polyethylene glycol surfactant, an associating oil, diindolylmethane, quercetin, and luteolin,
    the at least one monolayer surfactant bound particle has a ratio of the at least one amphiphilic fat to the polyethylene glycol surfactant from 1:1.8 to 1:3 by weight; and
  a continuous phase comprising glycerin, ethanol, and water;
  where
    the nanoemulsion is a stable dispersion that is transparent, and
    the at least one monolayer surfactant bound particle has an average particle diameter from 10 to 100 nanometers as carried by the continuous phase.

13. The method of claim 12, where the holding under the tongue is performed at least 20 minutes before a meal or at least 20 minutes after a meal.

14. The method of claim 12, where the from 4 to 6 milliliters of the nanoemulsion is approximately 5 milliliters.

15. The method of claim 12, where the 30 seconds to 2 minutes is approximately 30 seconds.

16. The method of claim 12, where a ratio of the diindolylmethane to the quercetin to luteolin in the at least one monolayer surfactant bound particle is 0.5:0.8:1 ±20%.

17. A method of making an intra-oral nanoemulsion for balancing histamine response in subjects when orally administered, the method comprising:
  forming a mixture comprising an amphiphilic fat chosen from phospholipid lecithin isolates and further comprising at least 30% by weight phosphatidylcholine, a polyethylene glycol surfactant, an associating oil, diindolylmethane, quercetin, luteolin, glycerin, ethanol, and water to form a nanoemulsion,
  where a ratio of the at least one amphiphilic fat to the polyethylene glycol surfactant is from 1:1.8 to 1:3 by weight; and
  stirring the nanoemulsion at room temperature and pressure to form a stable dispersion that is transparent and has an average particle diameter from 10 to 100 nanometers.

18. The method of claim 17, where the polyethylene glycol surfactant is chosen from TPGS, polysorbate 80, polysorbate 60, and combinations thereof.

19. The method of claim 17, where the polyethylene glycol surfactant is TPGS.

20. The method of claim 17, where the associating oil is chosen from medium chain triglycerides (MCT), citrus oil, and combinations thereof.

21. The method of claim 17, further comprising forming the mixture by combining at least one tocotrienol form of Vitamin E to form the nanoemulsion.

22. The method of claim 17, where the nanoemulsion is ingestible and edible.

23. The method of claim 17, where the average particle diameter of the nanoemulsion is from 10 to 60 nanometers.

24. The method of claim 17, where the ratio of the glycerin to the ethanol to the water in the continuous phase is 1.3:1:1.4 ±30% by weight.

25. The method of claim 17, where a ratio of the diindolylmethane to the quercetin to the luteolin in the nanoemulsion is 0.5:0.8:1 ±20%.

\* \* \* \* \*